US005851175A

United States Patent [19]

Nickell

[11] Patent Number: 5,851,175

[45] Date of Patent: Dec. 22, 1998

[54] SEXUAL ASSISTANCE DEVICE

[76] Inventor: William Kenneth Nickell, P.O. Box 745, Calvert City, Ky. 42029

[21] Appl. No.: 977,506

[22] Filed: Nov. 24, 1997

[51] Int. Cl.[6] .......... A61F 5/00

[52] U.S. Cl. .......... 600/38; 601/46

[58] Field of Search .......... 600/38, 39, 40, 600/41; 601/46

[56] References Cited

U.S. PATENT DOCUMENTS

| | | |
|---|---|---|
| 3,598,106 | 8/1971 | Bening . |
| 3,626,931 | 12/1971 | Bysakh . |
| 3,669,100 | 6/1972 | Csanad . |
| 3,991,751 | 11/1976 | O'Rourke . |
| 3,996,930 | 12/1976 | Sekulich . |
| 4,790,296 | 12/1988 | Segal . |
| 4,911,149 | 3/1990 | Borodulin et al. . |
| 5,063,911 | 11/1991 | Teranishi . |

*Primary Examiner*—John P. Lacyk
*Assistant Examiner*—Rosiland Kearney
*Attorney, Agent, or Firm*—Waddey & Patterson; Edward D. Lanquist, Jr.

[57] ABSTRACT

The present invention discloses a sexual assistance device having a base. A platform having a seat is connected to the base using a hinge. The seat has a slot in it which receives an elongated member such as a vibrator which is pivottally attached to the base. The user can then mount the seat and use the sexual assistance device to simulate the forward and rearward movement of the male penis during sexual intercourse.

14 Claims, 3 Drawing Sheets

SEXUAL ASSISTANCE DEVICE

BACKGROUND OF THE INVENTION

The present invention relates generally to a sexual assistance device and more particularly to a user ridden or mounted sexual assistance device.

It will be appreciated by those skilled in the art that sexual assistance devices are popular objects. Further, manufacturing and distribution of sexual assistance devices is a growing industry.

To this end, there have been several attempts to develop sexual assistance devices. The primary type of sexual assistance devices is a standard vibrator consisting of an elongated member having an internal vibrating means that can be controllable by a standard vibrator controller. To use such a device, the user must use one's own hand or have an assistant to assist in the usage. Unfortunately, such a device can only simulate sexual intercourse to a certain extent. Further, it appears to be primarily used to collect semen.

Another such attempt is disclosed in U.S. Pat. No. 4,790, 296. Unfortunately, this device is merely a box having a piston to which the vibrator or dildo is attached. Unfortunately, this does not simulate the forward and rearward movement occurring during sex.

Other devices are disclosed in U.S. Pat. Nos. 3,598,106; 3,626,931; 3,669,100; 3,991,751; 3,996,930; 4,911,149; and 5,063,911. Unfortunately, none of these accurately simulate sexual intercourse. Further, none of the devices are mountable systems.

What is needed, then, is a device which is simple to manufacture and to use. This device must be capable of simulating the forward and rearward movement of the male penis during sexual intercourse. This system must be readily portable. This needed device must be capable of simulating mounted intercourse. This needed device is presently lacking in the prior art.

SUMMARY OF THE INVENTION

The present invention discloses a sexual assistance device having a base. A platform having a seat is connected to the base using a hinge. The seat has a slot in it which receives an elongated member such as a vibrator which is pivottally attached to the base. The user can then mount the seat and use the sexual assistance device to simulate the forward and rearward movement of the male penis during sexual intercourse.

Accordingly, one object of the present invention is to provide a sexual assistance device.

Another object of the present invention is to provide a device which can simulate the forward and rearward movement of the male penis during sexual intercourse.

A further object of the present invention is to provide a device which is simple to manufacture and to access.

Another object of the present invention is to provide a portable device.

A further object of the present invention is to provide a system allowing the user to select the angle and depth of penetration.

DESCRIPTION OF THE PREFERRED EMBODIMENTS

Figure 1:
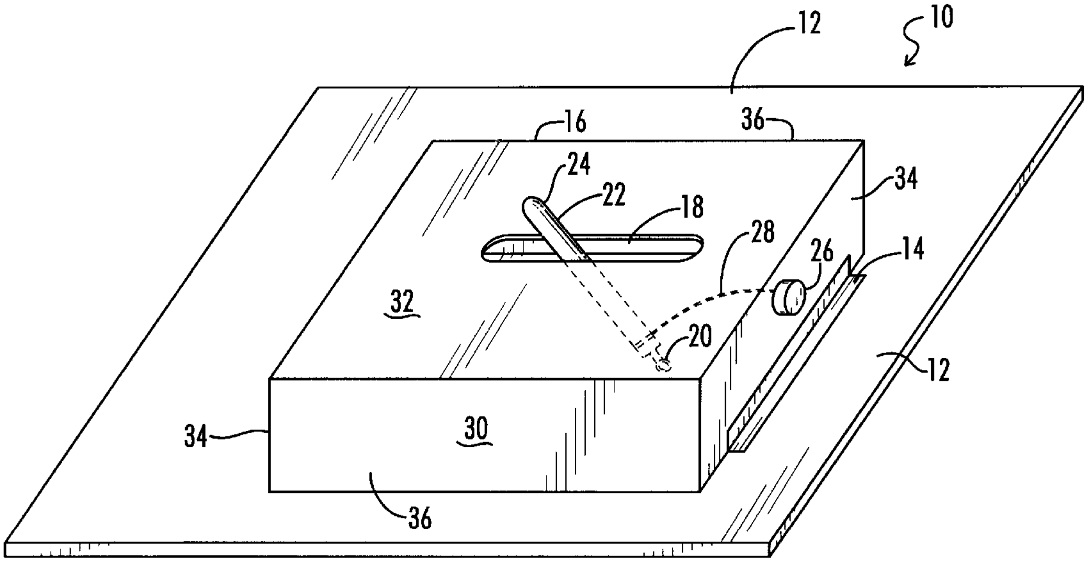
FIG. 1 is a perspective view of the preferred embodiment of the present invention.

Referring now to FIG. 1, there is shown at 10 the sexual assistance device of the present invention. Sexual assistance device 10 has base 12 and platform 16 which are joined together by hinge 14. Platform 16 has slot 18 which receives elongated member 22 which is, in the preferred embodiment, a vibrator. Elongated member 22 is attached to base 12 using pivot 20 which is shown in greater detail in FIG. 5. The combination of pivot 20 and slot 18 allows elongated member to arc or slide forward and backward along slot 18. In the preferred embodiment, clamp 70 can be released to allow vibrator 24 to be removed to allow user to change batteries or elongated member 22. In the preferred embodiment, elongated member 22 has external control 26 joined to vibrator 24 using wire 28. Control 26 is a standard vibrator control found on most vibrators which has merely been removed from vibrator and electrically attached using wire 28. In the preferred embodiment shown in FIG. 1, platform 16 has seat 32 supported by sides 36 and ends 34.

Figure 2:
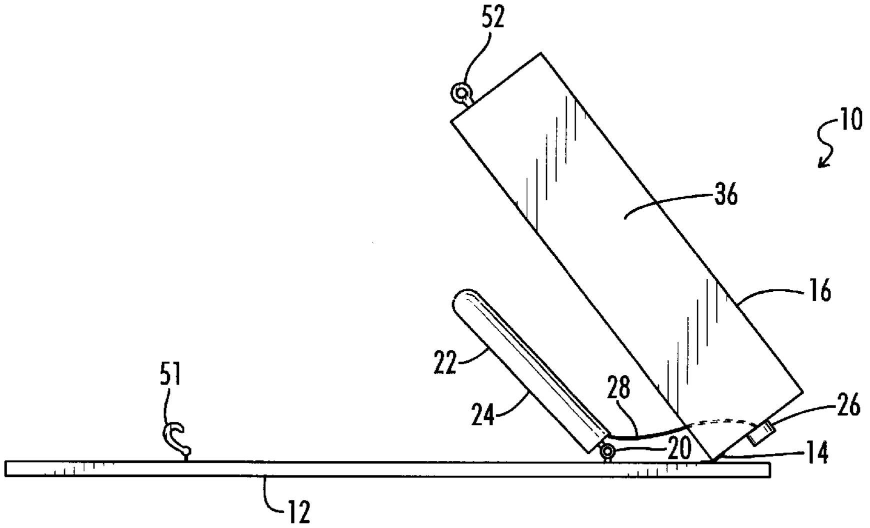
FIG. 2 is a side view of the preferred embodiment of the present invention showing the platform in an opened position.

Referring now to FIG. 2, one can see that hinge 14 allows platform 16 to be opened with respect to base 12. This allows access to elongated member 22 to do such things as exchange elongated member 22, change batteries in vibrator 24, or tighten pivot 20. Seat 32 is locked down by hook 51 and eye 52.

Figure 3:
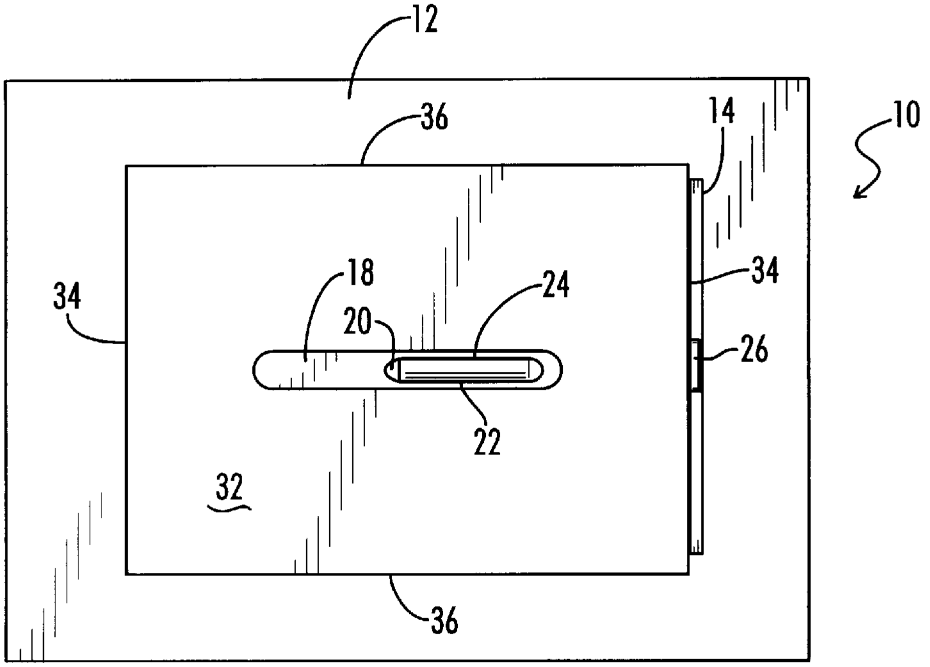
FIG. 3 is a plan view of the preferred embodiment of the present invention.

Referring now to FIG. 3, one can see more dearly how slot 18 and pivot 20 allows elongated member 22 to move in an arc fashion allowing user to select the preferred angle and amount of penetration desired.

Figure 4:
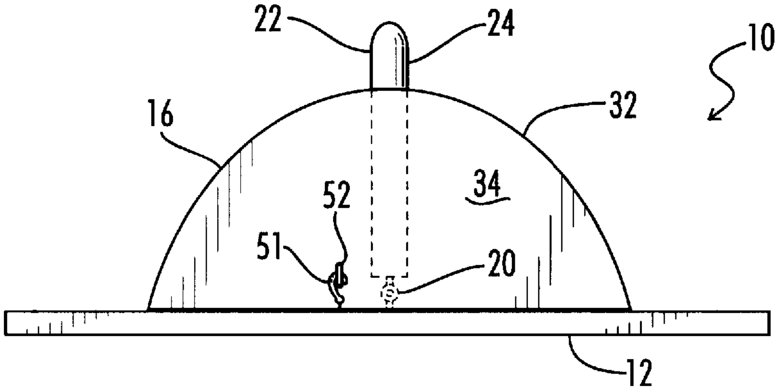
FIG. 4 is an end view of an alternate embodiment of the present invention having a curved seat.

Referring now to FIG. 4, there is shown generally at 10 still another embodiment of the present invention. In this particular embodiment, platform 16 has curved seat 32 joining ends 34. Although not shown in this view, curved seat 32 also has slot 18 similar to that shown in FIG. 1 to receive elongated member 22 which is preferably vibrator 24. Preferably, in the embodiment shown in FIG. 4, hinge (14 not shown in FIG. 4) is also used to access elongated member 22. Curved seat 32 is locked down by hook 51 and eye 52.

Device 10 can be covered with leather, cloth, or any other fabric. Device 10 can be constructed of any material such as plastic, metal, or wood.

In the preferred embodiment, controller 26 is a rotary or slide type controller in which vibrator 24 is activated by rotating or sliding controller 26 one notch from off. By rotating or sliding controller 26 further, vibrations from vibrator 24 are increased.

Storage of vibrator is achieved by opening platform and rotating vibrator such that vibrator is parallel to base then closing platform and latching.

Figure 5:
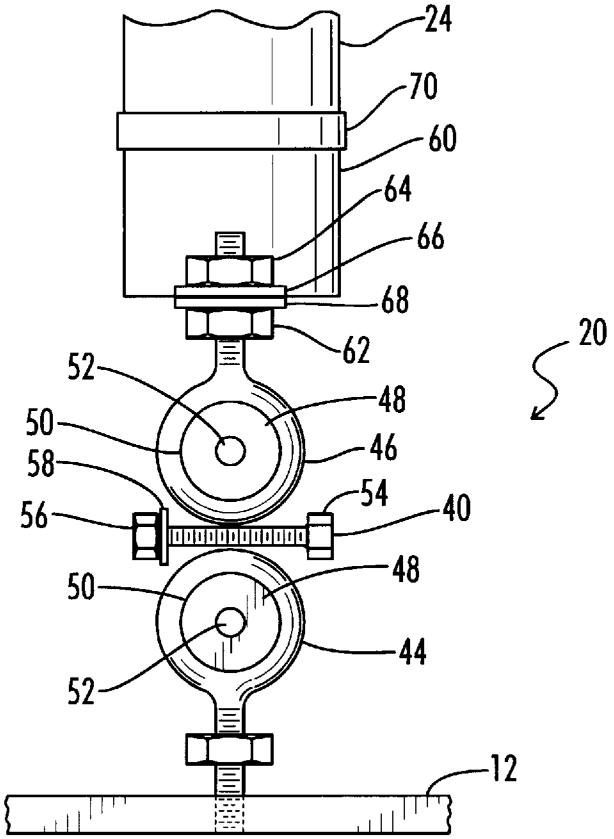
FIG. 5 is a frontal view of the pivot of the present invention.

FIG. 5 shows more detail for pivot 20. As can bee seen, pivot 20 consists of first eye bolt 44 and second eye bolt 46. Rubber grommets 48 are placed in each eyelet 50. Pin 40 is received by orifice 52 in grommets 48. Pin 40 consists of standard bolt 54 referenced as pin bolt 54 and pin nut 56 with pin washers 58. First eye bolt 44 is received by hole in base 12. Second eye bolt 46 is joined to end cap 60 which is attached to vibrator 24 by hose clamp 70. Nuts 62, 64 are used to attach eyebolt 44 to end cap 60 with washers 66,68 providing better attachment.

Thus, although there have been described particular embodiments of the present invention of a new and useful sexual assistance device, it is not intended that such references be construed as limitations upon the scope of this invention except as set forth in the following claims.

What is claimed is:

1. A sexual assistance device comprising:

a. a base;

b. a platform having a top portion and a bottom portion hingedly attached to said base, wherein said bottom portion contacts said base and said platform having a slot through said top portion;

c. an elongated member pivotally attached to said base and received by said slot.

2. The device of claim 1 further comprising means for vibrating said elongated member.

3. The device of claim 1 wherein said elongated member comprises a vibrator.

4. The device of claim 3 further comprising means for controlling said vibrator.

5. The device of claim 1 wherein said platform comprises a box.

6. The device of claim 1 wherein said platform comprises a box having a seat supported by two ends and a side.

7. The device of claim 1 wherein said platform comprises a curved seat.

8. The device of claim 1 wherein said platform comprises a curved seat joining two ends.

9. A sexual device comprising;

a. a base;

b. a hinge attached to said base;

c. a box-like platform attached to said base by said hinge, said platform having a top portion and a bottom portion contacting said base, said box-like platform having a seat supported by two ends and two sides, said seat having a slot; and d. an elongated member attached to said base by a pivot and received by said slot.

10. The device of claim 9 wherein said elongated member comprises a vibrator.

11. The device of claim 10 further comprising an external controller for said vibrator.

12. A sexual assistance device comprising:

a. a base;

b. a hinge attached to said base;

c. a platform attached to said base by said hinge, said platform having a curved seat supported by two ends, said seat having a slot; and d. an elongated member attached to said base by a pivot and received by said slot.

13. The device of claim 12 wherein said elongated member comprises a vibrator.

14. The device of claim 13 further comprising a remote controller for said vibrator.

* * * * *